United States Patent

Schäfer et al.

(10) Patent No.: US 6,689,914 B2
(45) Date of Patent: Feb. 10, 2004

(54) PREPARATION OF AMINES

(75) Inventors: Martin Schäfer, Grünstadt (DE); Arnd Böttcher, Frankenthal (DE); Andreas Kramer, Bad Dürkheim (DE); Arthur Höhn, Kirchheim (DE); Shelue Liang, Ludwigshafen (DE); Frank Funke, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/234,170

(22) Filed: Sep. 5, 2002

(65) Prior Publication Data

US 2003/0097021 A1 May 22, 2003

(30) Foreign Application Priority Data

Sep. 13, 2001 (DE) .......................... 101 45 119

(51) Int. Cl.$^7$ .............................. C07C 29/26
(52) U.S. Cl. ................. 564/480; 564/397; 564/398; 564/401; 564/472; 564/473; 564/479
(58) Field of Search ................ 564/397, 398, 564/401, 472, 473, 479, 480

(56) References Cited

U.S. PATENT DOCUMENTS

| 4,152,353 | A | * | 5/1979 | Habermann | 260/585 B |
|---|---|---|---|---|---|
| 4,153,581 | A | * | 5/1979 | Habermann | 252/472 |
| 4,254,060 | A | * | 3/1981 | Kimura et al. | 564/479 |
| 4,992,587 | A | * | 2/1991 | Koll | 564/398 |
| 5,331,101 | A | * | 7/1994 | Habermann | 564/480 |
| 6,187,957 | B1 | * | 2/2001 | Meyer et al. | 564/473 |
| 6,462,236 | B2 | * | 10/2002 | Liang et al. | 564/336 |

FOREIGN PATENT DOCUMENTS

DE 100 53380 5/2002

OTHER PUBLICATIONS

136:340479b—abstract of DE 10,053,380 (2000).

* cited by examiner

Primary Examiner—Brian Davis
(74) Attorney, Agent, or Firm—Keil & Weinkauf

(57) ABSTRACT

The preparation of amines of the formula (I):

$$R^1R^2CH-N\ R^3R^4 \qquad (I)$$

in which $R^1$, $R^2$, $R^3$ and $R^4$, independently of one another, are hydrogen, straight-chain or branched $C_1$–$C_{12}$-alkyl, $C_3$–$C_{12}$-cycloalkyl, $C_6$–$C_{10}$-aryl or $C_7$–$C_{11}$-aralkyl, takes place by catalytic, reductive amination of mixtures comprising carbonyl compounds of the formula (II) and/or alcohols of the formula (III)

$$R^1-C(=O)-R^2 \qquad (II)$$

$$R^1-CH(OH)-R_2 \qquad (III)$$

which also comprise at least 50 ppm, based on the mixtures, of halogen, with nitrogen compounds of the formula (IV):

$$H\ N\ R^3\ R^4 \qquad (IV)$$

with the abovementioned meanings for $R^1$ to $R^4$, in the presence of Co- and/or Ni-containing catalysts, which comprises carrying out the reductive amination additionally in the presence of solid acidic cocatalysts.

10 Claims, No Drawings

PREPARATION OF AMINES

The invention relates to a process for the preparation of amines by catalytic reductive amination of carbonyl compounds or alcohols which comprise halogen-containing impurities.

The reductive amination of carbonyl compounds with ammonia or primary or secondary amines is a standard process for the preparation of amines. The reaction is usually carried out in the presence of metallic catalysts, Raney-Ni, Raney-Co, Pt/activated carbon, Pd/activated carbon, $Pd/BaSO_4$, $Rh/Al_2O_3$, for example, being used as catalysts.

If the carbonyl compound to be aminated comprises, as a result of preparation, significant amounts of chlorine (for example >50 ppm), this leads to problems during reductive amination. Thus, for example, lower selectivities and space-time yields result, as does premature deactivation or destruction of the catalyst. In many cases, only partial conversion can be achieved, which hinders work-up. In particular, fixed-bed hydrogenations cannot be carried out economically in the presence of halogens or halogen-containing impurities due to disintegration of the catalyst.

In these cases, the carbonyl compound has to be purified prior to the amination in a complex manner. In many cases this is not economically feasible.

DE-A-100 53 380, which has an earlier priority date but was unpublished at the priority date of the present application, relates to a process for the preparation of amines by catalytic reductive amination of carbonyl compounds or alcohols which have at least one aromatic ring substituted by halogen which is not changed during the reductive amination. The hydrogenation is carried out in the presence of Co- and/or Ni-containing catalysts and solid acidic cocatalysts and in the absence of organic sulfur compounds.

It is an object of the present invention to provide a process for the simple and cost-effective preparation of amines by reductive amination of corresponding carbonyl compounds or alcohols which have a significant content of halogen (at least 50 ppm, in particular organically bonded), and which leads to the desired products with high space-time yields with low catalyst consumption.

We have found that this object is achieved according to the invention by a process for the preparation of amines of the formula (I):

$$R^1R^2CH{-}N\ R^3R^4 \quad (I)$$

in which $R^1$, $R^2$, $R^3$ and $R^4$, independently of one another, are hydrogen, straight-chain or branched $C_1$–$C_2$-alkyl, $C_3$–$C_{12}$-cycloalkyl, $C_6$–$C_{10}$-aryl or $C_7$–$C_{11}$-aralkyl, where at least one of the radicals $R^1$ and $R^2$ is aryl or aralkyl, by catalytic, reductive amination of mixtures comprising carbonyl compounds of the formula (II) or alcohols of the formula (III):

$$R^1{-}C({=}O){-}R^2 \quad (II)$$

$$R^1{-}CH(OH){-}R^2 \quad (III)$$

which also comprise at least 50 ppm, based on the mixtures, of halogen, with nitrogen compounds of the formula (IV):

$$H\ N\ R^3\ R^4 \quad (IV)$$

with the abovementioned meanings for $R^1$ to $R^4$ in the presence of Co- and/or Ni-containing catalysts, where the reductive amination is additionally carried out in the presence of solid acidic cocatalysts and optionally in the absence of organic sulfur compounds.

It has been found according to the invention that during the reductive amination of ketones, aldehydes or alcohols which are contaminated by significant amounts of halogen, it is possible to achieve very good amine yields if, during the reaction, the Co- and/or Ni-containing catalysts are used in combination with solid acidic cocatalysts.

The Co- and/or Ni-containing catalysts are preferably chosen from Raney-Co, Raney-Ni, Raney-Co—Ni, Raney-Ni—Fe, Raney-Ni—Fe—Co, Ni—Co mixed oxides, Ni/Co mixed oxides or mixtures thereof, which may also be on inorganic supports.

In addition, the Co and/or Ni catalysts can additionally comprise 0 to 80% by weight of Cu and 0 to 10% by weight, preferably 0 to 5% by weight, of further metals, calculated as metal and based on the total weight of the catalyst.

In the process according to the invention, the Co- and/or Ni-containing catalysts are preferably used in the form of elemental Co and/or Ni sponge, Raney-cobalt or Raney-nickel, Co or Ni or Co oxide or Ni oxide on supports (supported catalysts). They can also be used mixed in any weight ratios. Supports therefor are, for example, $Al_2O_3$, $SiO_2$, $TiO_2$, $ZrO_2$, activated carbon and other catalyst supports known to the person skilled in the art.

Of the Raney catalysts, preference is given to using Raney catalysts such as Raney-cobalt, Raney-cobalt-nickel, Raney-cobalt-nickel-iron, Raney-cobalt-nickel-iron-chromium or Raney-cobalt or Raney-nickel with dopings of other transition metals in anhydrous or else water-moist or solvent-moist form. Particular preference is given to using Raney-cobalt which comprises in each case 0 or 0.1 to 10% by weight; preferably up to 5% by weight of Al, Ni, Fe, Cr. The Co- or Ni-containing catalyst is used in an amount of from 0.01 to 20% by weight, preferably 0.1 to 10% by weight and particularly preferably 0.3 to 5% by weight, based on the carbonyl compound to be aminated.

According to the invention, it may also be preferred to use an Ni or Co-Ni catalyst which is supported on $ZrO_2$ and comprises 0 to 50% by weight of CuO, calculated as CuO and based on the total weight of the catalyst.

According to the invention, the solid acidic cocatalysts are preferably chosen from metal oxides or metal mixed oxides, zeolites, metal or ammonium salts of mineral acids or organic acids, acidic ion exchangers or mixtures thereof.

Preferred solid acidic cocatalysts in the process according to the invention are metal oxides, such as oxides or mixed oxides of the elements Zr, Ti, Cr, Mo, W, Mn, Fe, B, Al, Si, zeolites of natural and synthetic origin, metal or ammonium salts of strong mineral acids, such as hydrochloric acid, sulfuric acid, nitric acid, phosphoric acid, and of strong organic acids, such as formic acid, acetic acid, propionic acid and sulfonic acid, acidic ion exchangers, such as Nafion etc. In particular, $ZrO_2$ is used. The use amounts of the acidic cocatalysts are preferably between 0.1 and 20% by weight, preferably between 1–10% by weight, based on the carbonyl compound to be aminated.

If Co- or Ni-containing supported catalysts are used, the support materials such as $Al_2O_3$, $SiO_2$, $TiO_2$, $ZrO_2$ etc., may function as acidic cocatalysts. In this case, the addition of an additional acidic cocatalyst is not necessary. If the ammonium salts are used as acidic cocatalysts, then the conventional acid can be used directly instead of the ammonium salts. The ammonium salts then form as a result of the reaction of the acid with ammonia or amines.

In the process according to the invention, the acidic cocatalysts used are preferably metal oxides or mixtures thereof. Particular preference is given to $ZrO_2$.

The reductive amination can be carried out in a suspension operation or fixed-bed operation.

The carbonyl compounds or alcohols used according to the invention can be chosen with a large degree of freedom.

The aryl radicals and phenyl radicals and the aralkyl radicals are particularly preferably benzyl radicals. The alkyl radicals are preferably $C_{1-6}$-alkyl radicals, and the cycloalkyl radicals are preferably $c_{3-6}$-cycloalkyl radicals. It is particularly preferred that in the compounds of the formula (II) and (III), none of the radicals is hydrogen. In particular, the carbonyl compound is pinacolone or a derivative thereof.

The carbonyl compounds or alcohols to be aminated and used according to the invention comprise at least 50 ppm, particularly preferably 50 ppm to 10% by weight, in particular 100 ppm to 10% by weight, of halogen. The quantitative data refer here to a mixture of the carbonyl compounds or alcohols and to the halogen or halogen-containing compounds. The expression "halogen" and the quantitative data refer to halogen atoms present in the mixture, which may be in chemically bonded form or in the form of ions or salts. In particular, the halogen is organically bonded, i.e. the organic compounds contain the halogen atoms, in particular chlorine atoms, in chemically bonded form. The quantitative data refer, however, to the halogen itself, independently of the nature and size of the organic radical. The halogen is usually in the form of an ionic impurity or, in particular, bonded to organic impurities in the carbonyl compound used.

The mixture used according to the invention is thus, in particular, pinacolone or derivatives thereof contaminated with organic chlorine compounds.

The nitrogen compound of the formula (IV) is preferably ammonia or primary or secondary aliphatic amines. The latter preferably have $C_{1-6}$-alkyl radicals. Ammonia is particularly preferably used as nitrogen compound.

The amination in the process according to the invention can be carried out in solvents, for example alcohols, such as methanol, ethanol, propanol, butanol, aliphatic or aromatic hydrocarbons, such as toluene, xylene, cyclohexane, isooctane, ethers, such as tetrahydrofuran, dioxane, methyl tert-butyl ether. In a preferred embodiment, however, no additional solvent is used, but the aminating agent (ammonia or amines) used in excess acts as a solvent at the same time. The molar ratio of ammonia or amine to carbonyl compound is preferably greater than 1, and for rapid reactions is preferably greater than 2.

The amination is preferably carried out at a temperature at from 10 to 250° C., preferably from 40 to 150° C. and at a pressure of from 10 to 200 bar, preferably from 30 to 130 bar.

The process according to the invention can be carried out in a fixed-bed, but also, for example, in an autoclave in suspension, as is described below. The Co- or Ni-containing and the acidic cocatalysts and the carbonyl compound are introduced into the reactor in any order under a protective gas. Ammonia or amines are metered in at room temperature with stirring. The mixture is heated to the reaction temperature and then hydrogen is injected in up to the reaction pressure. When the hydrogen absorption has ended, the reactor is cooled to room temperature, decompressed and emptied. The catalysts are filtered off and reused for the next reaction cycle. The reaction product is then worked up in a manner known to the person skilled in the art.

The process can be carried out either discontinuously, for example in an autoclave, and also continuously, for example in a pressurized reactor with attached separator and pressure release.

The use of Co- and/or Ni-containing catalysts in combination with acidic cocatalysts permits the reductive amination of halogen-containing starting materials; it is possible to achieve high space-time yields with only slight catalyst losses. The high amine selectivities and yields in the process according to the invention, combined with simple implementation of the synthesis permit simple work-up and thus, overall, an economic preparation process.

The process according to the invention is described in more detail by reference to the examples below using pinacolone (3,3-dimethylbutanone) as a representative carbonyl compound.

EXAMPLES

The pinacolone used in the examples had a purity of >98.4% (according to GC), and the content of organically bonded halogen was 280 ppm. The catalysts used in the process are likewise commercially available products with the following composition:

| | |
|---|---|
| Ra—Ni: | Raney-nickel, suspension catalyst |
| $Al_2O_3$ | Powder |
| $ZrO_2$: | Powder |

The amination experiments were carried out in accordance with the general procedure below and are not optimized. It may therefore be possible to achieve higher amine selectivities and yields.

General Procedure:

The catalyst, pinacolone (Cl content (organically bonded): 280 ppm) and, as solvent, methanol are introduced into a 2.5 l autoclave, flushed and filled with nitrogen, fitted with a disk stirrer and two wave-breakers. At room temperature and with stirring (500 rpm), ammonia is firstly injected in, followed by hydrogen to a pressure of 20 bar. The mixture is heated to the reaction temperature, injected with fresh hydrogen to the reaction pressure and then stirred under a constant hydrogen pressure. After the absorption of hydrogen has ended, the autoclave is cooled, decompressed, degassed and emptied. The compositions of the reaction products are determined by gas chromatography. The experimental results are summarized in Table 1.

TABLE 1

Results of the amination of pinacolone (3,3-dimethylbutanone)

| Example | Catalysts (g) | Pinacolone/ $NH_3$/MeOH [g] | T/P [° C./bar] | Conversion [%] | Amine [%] | Alk[a] [%] | SB[b] [%] | Time/h |
|---|---|---|---|---|---|---|---|---|
| 1 | Ra—Ni(15)/$ZrO_2$ (25) | 500/255/250 | 150/180 | 97 | 94 | 0.6 | 1.2 | 30 |
| C2 | Ra—Ni(15) | 500/255/250 | 150/180 | 72 | 59 | 0.5 | 10.9 | 30 |
| 3 | Ra—Ni (6)/$ZrO_2$ (15) | 300/170/150 | 110/100 | 94 | 86 | 2 | 5 | 30 |

C2 = Comparative example
[a]Alk. = 3,3-dimethylbutanol,
[b]SB = Schiff's Base of 3,3-dimethylbutanone and 3,3-dimethylbutylamine.

The above experimental results show that using the acidic cocatalysts it was possible to achieve considerably higher conversions and product selectivities.

We claim:

1. A process for the preparation of amines of the formula (I):

$$R^1R^2CH\text{—}N R^3R^4 \qquad (I)$$

in which $R^1$, $R^2$, $R^3$ and $R^4$, independently of one another, are hydrogen, straight-chain or branched $C_1$–$C_{12}$-alkyl, $C_3$–$C_{12}$-cycloalkyl, $C_6$–$C_{10}$-aryl or $C_7$–$C_{11}$-aralkyl, by catalytic, reductive amination of mixtures comprising carbonyl compounds of the formula (II) and/or alcohols of the formula (III):

$$R^1\text{—}C(=O)\text{—}R^2 \qquad (II)$$

$$R^1\text{—}CH(OH)\text{—}R^2 \qquad (III)$$

which also comprise at least 50 ppm, based on the mixtures, of halogen, with nitrogen compounds of the formula (IV):

$$H N R^3 R^4 \qquad (IV)$$

with the abovementioned meanings for $R^1$ to $R^4$, in the presence of Co- and/or Ni-containing catalysts, which comprises carrying out the reductive amination additionally in the presence of solid acidic cocatalysts.

2. A process as claimed in claim 1, wherein the solid acidic cocatalysts are chosen from metal oxides or metal mixed oxides, zeolites, metal or ammonium salts of mineral acids or organic acids, acidic ion exchangers or mixtures thereof.

3. A process as claimed in claim 1, wherein the Co- and/or Ni-containing catalysts are chosen from Raney-Co, Raney-Ni, Raney-Ni—Fe, Raney-Ni—Fe—Co, Ni mixed oxides, Co mixed oxides, Ni/Co mixed oxides or mixtures thereof, which may also be on inorganic supports.

4. A process as claimed in claim 1, wherein the Co- and/or Ni-containing catalysts additionally comprise 0 to 80% by weight of Cu and 0 to 10% by weight of further metals, calculated as metal and based on the total weight of the catalyst.

5. A process as claimed in claim 4, wherein a Raney-Ni catalyst is used which additionally comprises in each case 0 to 10% by weight of Al, Co, Cr and/or Fe, calculated as metal and based on the total weight of the catalyst.

6. A process as claimed in claim 4, wherein an Ni catalyst is used which is supported on $ZrO_2$ and comprises 0 to 50% by weight of CuO, calculated as CuO and based on the total weight of the catalyst.

7. A process as claimed in claim 1, wherein the solid acidic cocatalysts used are oxides and mixed oxides of the elements Zr, Ti, Cr, Mo, W, Mn, Fe, B, Al, Si or mixtures thereof, zeolites, metal or ammonium salts of hydrochloric acid, sulfuric acid, nitric acid, phosphoric acid or formic acid, acetic acid, propionic acid or sulfonic acid or acidic ion exchangers.

8. A process as claimed in claim 7, wherein the solid acidic cocatalyst used is $ZrO_2$.

9. A process as claimed in claim 1, wherein the catalysts and cocatalysts are used in suspension.

10. A process as claimed in claim 1, wherein pinacolone is used as carbonyl compound and ammonia is used as nitrogen compound.

* * * * *